United States Patent [19]
Günther et al.

[11] Patent Number: 5,747,534
[45] Date of Patent: May 5, 1998

[54] LOBAPLATIN TRIHYDRATE

[75] Inventors: Eckhard Günther, Offenbach; Jens-Peter Wulf, Maintal; Jürgen Engel, Alzenau; Bernhard Kutscher, Maintal, all of Germany

[73] Assignee: Asta Medica AG, Germany

[21] Appl. No.: 714,456

[22] Filed: Sep. 16, 1996

Related U.S. Application Data

[63] Continuation of PCT/EP95/01214, Mar. 31, 1995, published as WO95/28407, Oct. 26, 1995.

[30] Foreign Application Priority Data

Apr. 15, 1994 [DE] Germany ............ 44 15 263.9

[51] Int. Cl.$^6$ ............ A61K 31/295; C07F 15/00
[52] U.S. Cl. ............ 514/492; 556/137
[58] Field of Search ............ 556/137; 514/492

[56] References Cited

U.S. PATENT DOCUMENTS 5,023,335  6/1991  Schumacher et al. ............ 548/104

FOREIGN PATENT DOCUMENTS

| | | |
|---|---|---|
| 4115559 | 11/1991 | Germany. |
| 1083911 | 1/1980 | U.S.S.R. |
| 1186617 | 8/1981 | U.S.S.R. |
| 1414850 | 5/1983 | U.S.S.R. |

OTHER PUBLICATIONS

Morikawa et al. Synthesis, Antitumor Activity, and Nephrotoxicity of the Optical Isomers of 2–Aminomethylpyrrolidine (1,1–cyclobutane–dicarboxylato) platinum (II)–vol. 80, No. 9, Sep. 1991 p. 837.

Guchelaar et al., CA Abstract—Stability of the new anticancer platinum analog 1,2–diaminomethyl–cyclobutane–platinum (II)–lactate (lobaplatin;D19466) in intravenous solutions, vol. 117, CA Abstract No. 763356, 1992.

*Primary Examiner*—Porfirio Nazario-Gonzalez
*Attorney, Agent, or Firm*—Schweitzer Cornman Gross & Bondell LLP

[57] ABSTRACT

Cis-[trans-1,2-cyclobutanebis (methylamine)-N,N']-[(2S)-lactate-$O^1,O^2$)-platinum (II) trihydrate (lobaplatin trihydrate) and its preparation.

6 Claims, No Drawings

LOBAPLATIN TRIHYDRATE

This is a continuation of the parent U.S. patent application PCT/EP95/01214, Mar. 31, 1995, published as WO95/28407, Oct. 26, 1995.

FIELD OF THE INVENTION

The present invention relates lobaplatin trihydrate and to a method for its preparation.

Background of the Invention

Platinum complexes of 1,1-bis (aminomethyl)-cyclobutane, for example, are known from UK patent application No. 2,024,823. These compounds are recommended for treatment of cancer. The compounds according to that patent have a good antitumor activity (for example (in vitro on AH 135 tumor, B 16 melanoma, colon 115; in vivo, for example, on P 388 leukemia in mice). Furthermore, the compounds of that UK patent application have only a low toxicity, and in particular they have no cumulative toxicity and no nephrotoxicity.

European patent No. 324,154 describes platinum complexes of trans-1,2 bis (aminomethyl) cyclobutane as compounds having a potent antitumoral action. In particular, cis-[trans-1,2-cyclobutanebis (methylamine)-N,N']-[(2S)-lactato-$O^1,O^2$]-platinum (II) (INN: lobaplatin) has proved to have a better action and better tolerability than cisplatin (R. Voegeli et al. Drugs of the Future 1992, 17, 883–886 and R. Voegeli et al., J. Cancer Res. Clin. Oncol., 1990, 116, 439–442).

Chemical synthesis of lobaplatin has in the prior art been directed preparation of the anhydrous substance, such as can be seen from the synthesis example of European patent No. 324,154, Example 1a, where the aqueous reaction solution was completely concentrated the residue was taken up in methanol, the mixture was stirred with active charcoal and the filtrate was crystallized at refrigerated temperature, after addition of diethyl ether. The crystals thus obtained were vacuum-dried. There are difficulties with this procedure in reproducibly adjusting the purity and content parameters. Furthermore, the substance is hygroscopic and presents difficulties in metering and galenical processing due to agglutination.

SUMMARY OF THE INVENTION

The object of the invention is to provide a new form of lobaplatin which is easier and more reliable to handle and which has an improved quality. It is furthermore important to provide hospital personnel with a galenical form which is easy to handle, since handling of cytostatics is not without industrial hygienic problems.

It has now been found that a trihydrate of lobaplatin fulfills the above-mentioned requirements to a high degree. Hydrated forms of lobaplatin are not known from the literature. A targeted experimental investigation has now shown that the trihydrate of lobaplatin has surprisingly meaningful advantages.

DETAILED DESCRIPTION

The present invention describes the isolation of lobaplatin as the trihydrate and the resulting unexpected advantages: easier synthesis, reduction in of the by-products, no hygroscopy, reproducibly adjustable water content, improved storage stability, easier metering, better pharmaceutical processability. Galenical formulations can be easily prepared by the finishing of pharmaceutical compositions containing lobaplatin trihydrate as active ingredient, such as in the form of tablets, capsules, coated tablets, sustained-release formulations, lyophilizates or injection or infusion solutions.

The following examples demonstrate these advantages:

1. Synthesis

Lobaplatin is synthesized completely analogously to Example 1a of European patent No. 324,154 with dropwise addition of the dihydroxo-platinum complex into the aqueous lactic acid solution and working of up in the following simpler manner. Crude lobaplatin is crystallized out after concentration of the aqueous reaction batch, and is recrystallized from a water/acetone mixture with the addition of a small amount of active charcoal. The crystals thus obtained as the trihydrate, are dried in air at room temperature or slightly elevated temperature.

An analytical profile which shows the clear superiority of the substance synthesized as the trihydrate was established from 15 batches, 7 batches having been prepared as the anhydrous substance, and 8 batches as the trihydrate.

2. Elemental Analysis

| calculated | found | deviation* |
|---|---|---|
| a) Anhydrous: | | |
| C 27.21% | 25.86% | 5.0% |
| H 4.57% | 4.82% | 5.5% |
| N 7.05% | 6.65% | 5.7% |
| Pt 49.10% | 46.39% | 6.1% |
| b) Trihydrate: | | |
| C 23.95% | 23.92% | 0.1% |
| H 5.36% | 5.25% | 2.1% |
| N 6.21% | 6.06% | 2.3% |
| Pt 43.22% | 43.44% | 0.5% |

*deviation = 100% × (calculated − found)/calculated

3. Content Assay a) Of Anhydrous Lobaplatin

The water content values of 3.73±1.55% were determined by means of Karl-Fischer titration and show that complete drying was not possible because of the hygroscopy of lobaplatin. Furthermore, the values achieved have a very wide scatter.

According to the prescribed specification, the active compound content must be between 97% and 102%. The active compound content determined by means of HPLC (minus the water content values determined by Karl-Fischer titration), at an active compound content of 98.00±1.38%, were below the values required according to the specification and likewise had a wide scatter.

b) Of Lobaplatin Trihydate

The water content of the trihydrate batches, at 12.09±0.09%, were very close to the theoretical value of 11.96%. The analyses of the active compound content assay also reached acceptable values with 99.76±0.83%, the variations of which lie within the customary pharmaceutical limits.

4. Impurities Profile

The content of known and unknown impurities was determined by thin layer chromatography. The total of the impurities was determined as 1.21±0.55% for the anhydrous substance, and as 0.34±0.19% for the trihydrate. Here also, both the absolute values and scatter were improved.

5. Turbidity

Improvements were also achieved for the turbidity values measured: while these were 1.45±0.91 FTU for the anhydrous substance, it was possible to achieve 0.38±0.41 FTU with the trihydrate.

6. Stability

In each case two batches of anhydrous substance and trihydrate were stored in storage studies in each case at 4° C., room temperature, 31° C., 41° C. and a 31° C. at 80% relative atmospheric humidity (open sample bottles). After 3, 6 and 12 months, the impurities profiled (TLC), the active compound content (HPLC), the water content (Karl-Fischer titration) and the turbidity were investigated. The following was found for all the storage conditions:

The impurities content increased in the case of the substance prepared under anhydrous conditions. In the case of the trihydrate, the impurities were at a constant low level.

The active compound content is clearly closer to the 100% value, with less scatter, in the case of the trihydrate.

The hygroscopic, anhydrous substance shows an increase in the water content, while this is constant in the trihydrate according to the invention.

The turbidities of the lyophilized batches prepared in accordance with the instructions provided in German published application No. 3,843,571, from the anhydrous substance start at significantly higher values and increases substantially further during storage. In the trihydrate batches, the turbidity values remain at a constant low level.

7. Pharmaceutical Processing

Due to the hygroscopy of the anhydrous compound, it must be handled as far as possible with the exclusion of air. Agglutination and adhesion readily occur on the entry of moisture. The air-stable trihydrate is distinguished by good free-flowing properties and therefore significantly improved ease of metering and processability.

Further Examples of Preparation of Lobaplatin Trihydrate 3.8 g (10 mmol) of cis-[trans-1,2-cyclobutanebis-(methylamine)-N,N']dichloroplatinum (II) are suspended in 20 ml of water and the suspension is heated to 40° C. 3.39 g (20 mmol) of silver nitrate are added. After the mixture has been stirred for 1.5 hours and cooled in a refrigerator, the silver chloride which has precipitated out is filtered off with suction and washed with 10 ml of water. The filtrate is passed over a column containing 100 ml of a basic ion exchanger and rinsed with 150 ml of water. Any commercially available basic ion exchanger can be employed as the ion exchanger. The product is added dropwise to 4.5 g (10 mmol, 20% strength) of L-lactic acid. After the mixture has been stirred for three days, it is concentrated to about 20 ml and the concentrate is left to stand overnight in a refrigerator. The crystals which have precipitated out are filtered off with suction, the filtrate is concentrated further and the crystals which have precipitated out after the concentrate has stood overnight in a refrigerator are again filtered off with suction. The combined amounts of crystals are recrystallized from 20 ml of water/acetone (1/1, v/v). Yield 2.3 g (51%), melting point 210° C. (decomposition).

$C_9H_{24}N_2O_6$ Pt M=451.38 Calculated: C 23.95% H 5.36% N 6.21% Pt 43.22% Found: C 23.94% H 5.28% N 6.15% Pt 43.05% C 23.99% H 5.25% N 6.05% Water content (Karl-Fischer titration): 12.24% (calculated 11.96%) $^1$H-NMR (500 MHZ, $D_2O$): δ (ppm)=1.2 (d, 3H, $CH_2$), 2.4 (m, 2H, $CH_2$—$NH_2$), 4.05 (q, 1H, $CH$—$CH_3$), 4.3 . . . 5.0 (br. overlapped, $NH_2$)

We claim:

1. Cis-[trans-1,2-cyclobutanebis (methylamine)-N,N']-[(2S)-lactate-$O^1,O^2$)-platinum (II) trihydrate.

2. A pharmaceutical composition containing an active ingredient cis-[trans1,2-cyclobutanebis (methylamine)-N, N']-[(2S)-lactate-$O^1,O^2$]-platinum (II) trihydrate together with conventional pharmaceutical excipients, diluents, or auxiliaries.

3. A process for treating cancer of a host, which comprising administering to a host in need therefor an antitumor effective amount of the pharmaceutical composition of claim 2.

4. A process for preparing the compound of claim 1, which comprises recrystallizing cis-[trans-1,2-cyclobutanebis (menthylamine)-N'N"]-[(2S)-lactato-$O^1$, $O^2$]-platinum (II), from an aqueous medium to obtain the trihidrate end product.

5. The process of claim 4, wherein said aqueous medium is a water/acetone mixture.

6. The process of claim 5, wherein said mixture comprises approximately 1 part v/v of water per like part of acetone.

* * * * *